United States Patent [19]

Starr, Jr.

[11] Patent Number: 4,466,274
[45] Date of Patent: Aug. 21, 1984

[54] SLIDING FILM RHEOMETER

[76] Inventor: Frank C. Starr, Jr., 2010 Harvey Rd., Wilmington, Del. 19810

[21] Appl. No.: 392,727

[22] Filed: Jun. 28, 1982

[51] Int. Cl.³ .......................................... G01N 11/04
[52] U.S. Cl. ....................................................... 73/54
[58] Field of Search ........................................... 73/54

[56] References Cited

U.S. PATENT DOCUMENTS 2,849,875  9/1958  DeMaria ................................. 73/54

Primary Examiner—Gerald Goldberg
Assistant Examiner—Joseph W. Roskos
Attorney, Agent, or Firm—Abramo & Abramo

[57] ABSTRACT

A sliding film rheometer for measuring the viscosity of a molten polymer comprising a measuring cell containing a molten polymer, the cell having a rectangular slit through which is passed a rectangular shaped tape at a constant rate and strain gauges connected to the measuring cell for measuring the shear stress and normal stress produced by pulling the rectangular shaped tape through the molten polymer and through the slit from which the viscosity is calculated. The viscosity measurement provides useful data for obtaining optimum extrusion of said molten polymers.

6 Claims, 9 Drawing Figures

SECTION 3'-3" THRU FIG. 1

SECTION 2'-2" THRU FIG. 1

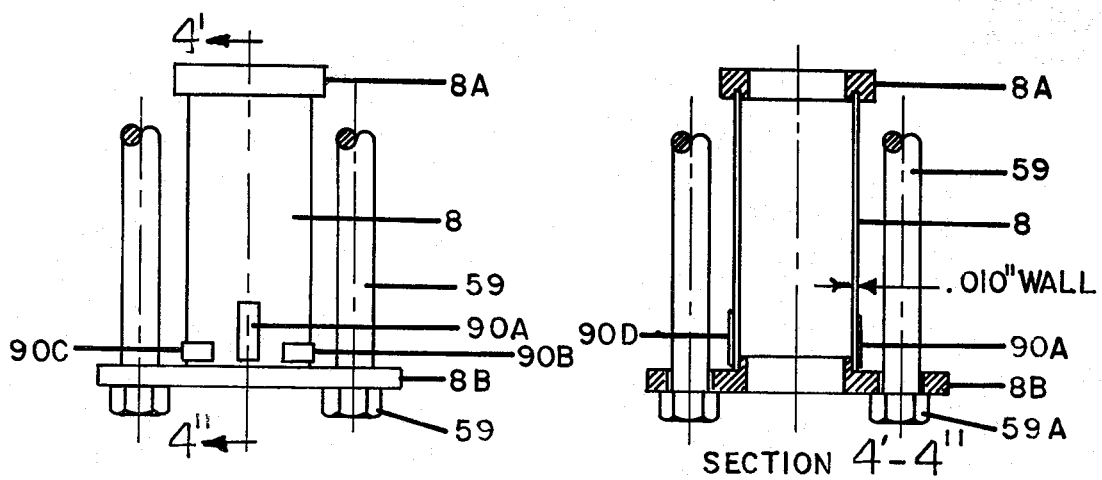
Figure 6
Figure 7
SECTION 4'-4" THRU FIG. 6
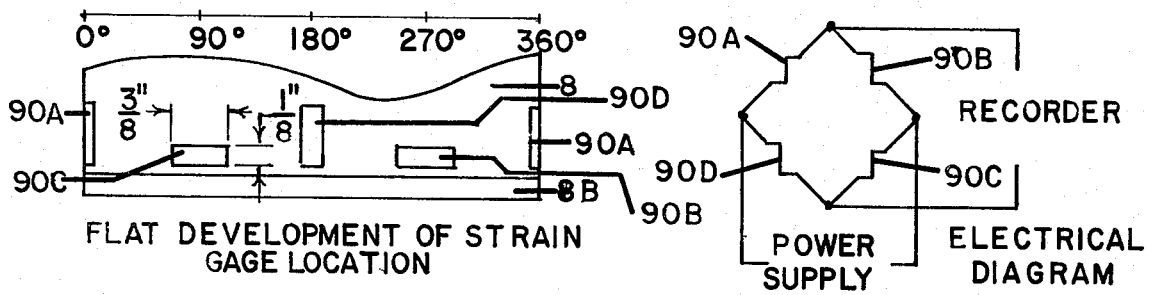
Figure 8
FLAT DEVELOPMENT OF STRAIN GAGE LOCATION
Figure 9
ELECTRICAL DIAGRAM

SLIDING FILM RHEOMETER

BACKGROUND OF THE INVENTION (a) Field of the Invention

This invention relates to an apparatus for measuring physical properties of molten polymers and resins. More specifically, this invention is directed to a rheometer for measuring the physical properties of polymers and resins in the molten state.

(b) The Prior Art

Over the years in addition to the melt indexer there have been a number of rheometers for the examination of polymer melts, plate and plate, cone and plate, cone and cone, etc. Other than the melt indexer all these were cumbersome, difficult to operate, poor in reproducibility, time consuming and, in most cases, the data obtained was difficult to interpret.

In this invention the data is readily obtained and a wide range of shear rates may be determined in a minimum of time, each determination covering but a few seconds. The determinations are made in a homogenous shear field with neglible end effects.

Both the shear stress and the normal stress are measured simultaneously in the same shear field. Due to the slit die design of this invention, the polymer properties can be obtained at negligible thermal gradient with rapidity of determination. In addition, thin polymer films are obtained by stripping from the steel tape which provides additional data about the polymer or resin.

In previously developed rheometers a number were difficult to operate; some requiring special training, and most required considerable time per determination and disassembly and cleaning between determinations.

It is the object of this invention to provide a rheometer which is capable of easy operation and which provides rapidity of individual determinations.

It is a further object of this invention to provide a rheometer which may be operated for long periods of time without cleaning or disassembly. In addition, it is the object of this invention to provide a useful end product of each determination, namely a thin polymer film which may be critically examined either photographically or optically, and thereby provide additional information about the polymer.

SUMMARY OF THE INVENTION

This invention is directed to a rheometer for measuring the viscosity of a molten polymer by measuring shear stress and normal stress of the molten polymer comprising:

(i) a shear stress and normal stress producing member;

(ii) a measurung cell connected to a source of molten polymer through which the shear stress and normal stress producing member is pulled;

(iii) control means to pull the shear stress and normal stress producing members through the molten polymer in the measuring cell; and (iv) means for measuring shear stress and normal stress produced by pulling the shear stress and normal stress producing members through the molten polymer.

This invention is more particularly directed to a rheometer for measuring shear stress and normal stress comprising:

(i) a tape;

(ii) a measuring cell connected to a source of molten polymer heated to a constant temperature;

(iii) control means to pull the tape through the measuring cell and molten polymer at a controlled rate of speed;

(iv) shear measuring means for measuring shear forces produced by pulling the tape through the molten polymer operatively connected to said measuring cell; and (v) stress measuring means for measuring stress force produced by pulling the tape through the molten polymer.

An object of this invention is a rheometer capable of determining the viscosity characteristics of a molten polymer by measuring the shear stress and normal stress produced in said molten polymer comprising a shear stress and normal stress producing member which is pulled at a controlled rate through a measuring cell having a close fitting orifice in a measuring cell containing the molten polymer which causes a microdisplacement of the measuring cell in the direction of pull and means for measuring the force of displacement of the measuring cell; said measuring cell containing a diaphragm located at the point of close fitting thereby causing a microflexing of the diaphragm, means for measuring said microflexing of the diaphragm wherein said shear stress and normal stress are calculated from the force of displacement and the amount of microflexing.

This invention is also directed to a process of determining polymer flow characteristics by cooling to the solid state molten polymer adhering to the shear stress and normal stress producing member, stripping said solid polymer from said menber and visually characterizing said polymer.

An object of this invention is the process of measuring the viscosity of a molten polymer or highly viscous material using the rheometer disclosed herein.

BRIEF DESCRIPTION OF THE DRAWINGS

FIG. 6 is a front elevational view of the measuring cell of the rheometer shown in FIG. 1;

FIG. 7 is a cross-sectional view of the measuring cell shown in FIG. 6 along line 4—4;

FIG. 8 is a diagram showing the flat development of the location of strain gauges on the measuring cell of FIG. 6; and FIG. 9 is a schematic showing the electric connection of the strain gauge.

DESCRIPTION OF THE PREFERRED EMBODIMENTS

Figure 1:
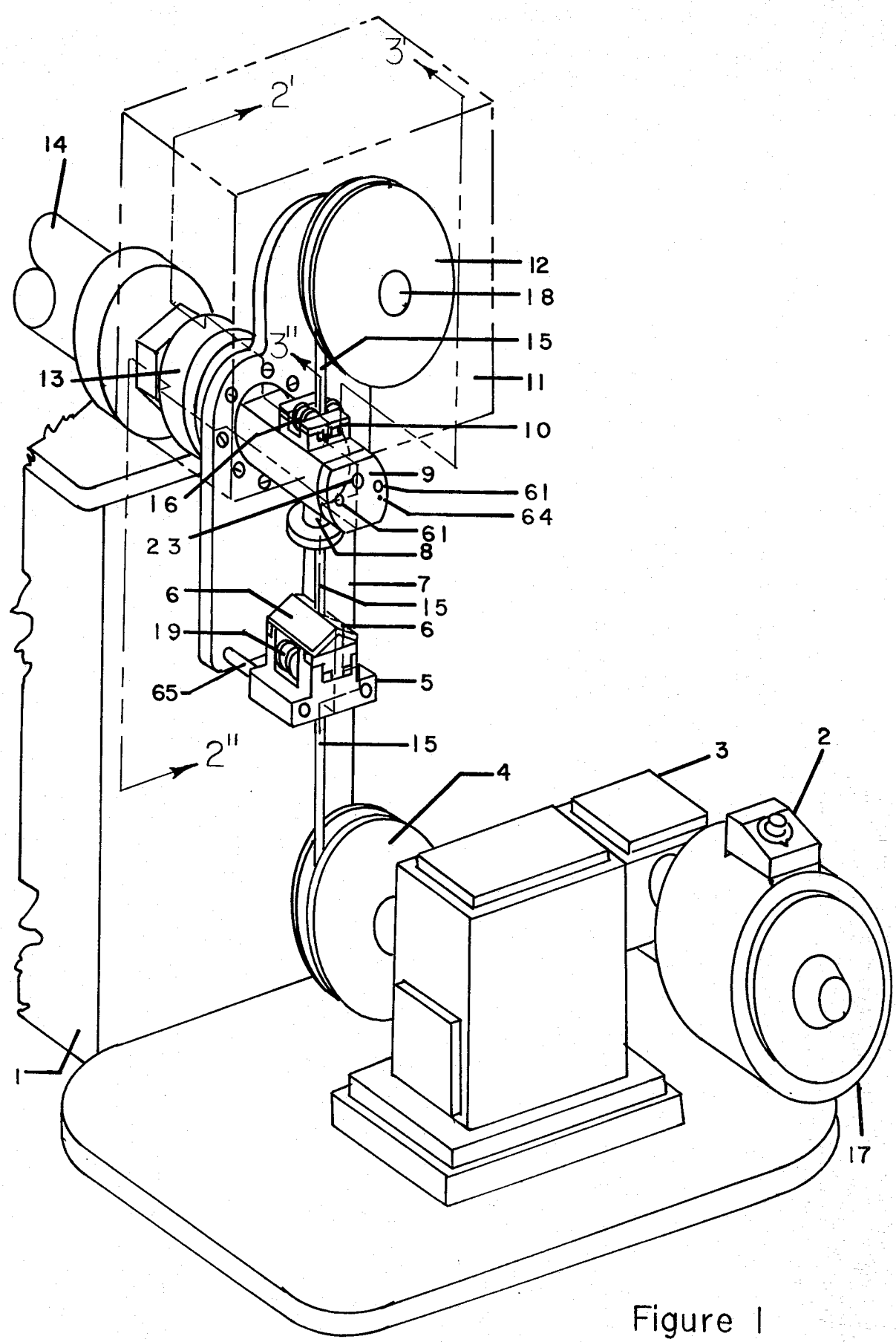
FIG. 1 is a pictoral view of the sliding film rheometer described and claimed herein.
Figure 3:
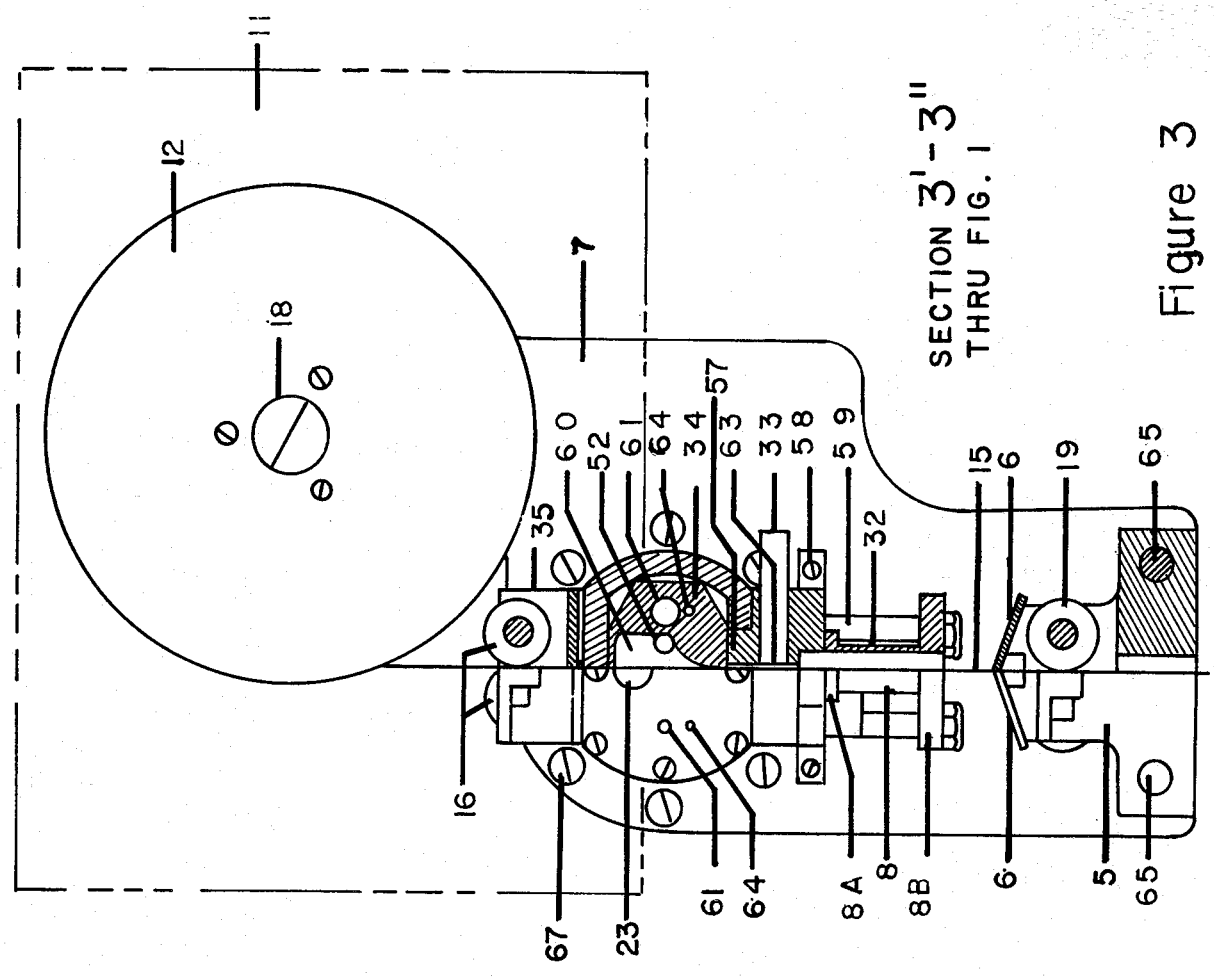
FIG. 3 is a composite cross-section front elevational view of the rheometer of FIG. 1 partially broken away along line 3—3.
Figure 2:
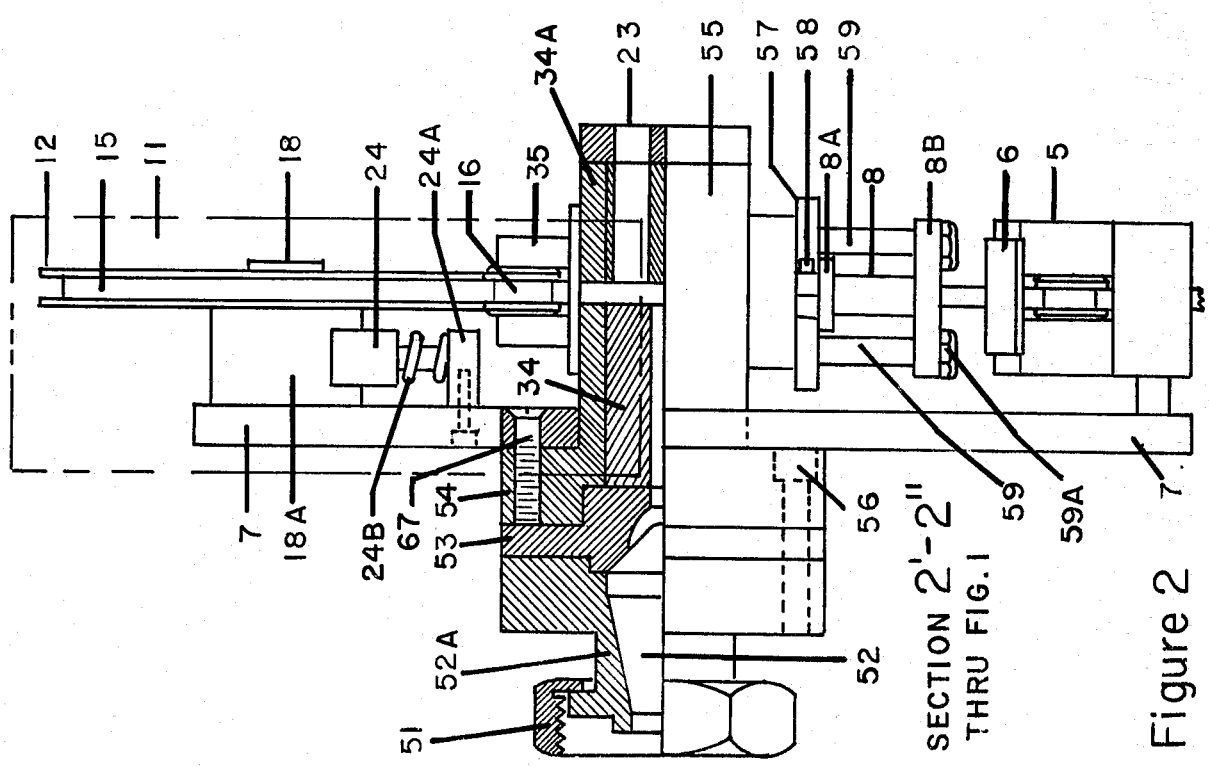
FIG. 2 is a composite cross-section side elevational view of the rheometer of FIG. 1 partially broken away along line 2—2.

Referring to the drawings and more specifically in FIGS. 1 through 9, it will be seen that the sliding film rheometer 1 is positioned at the exit port 14 of a molten polymer or molten resin extruder upon which is placed an adapter 13 to which is attached a measuring stage 8 where molten polymer to be studied flows through the measuring stage and then out of the measuring stage through excess polymer exit 23 in a temperature leveling case 9 attached to the end of the measuring stage. Positioned above the measuring stage in a support frame 7 is a stainless feed spool 12 containing a thin stainless steel tape 15. The spool 12 is heated to a desired temperature by a spool heater 11 (shown in phantom). Said spool 12 freely rotates upon a hub 18 attached to said frame. The tape is guided through the measuring stage by means of a roller guide 10 positioned on top of the measuring stage and having upper roller alignment guides 35.

The tape is drawn through the measuring stage onto a tape take up spool 4, the speed of which is controlled by a high torque reducer 3 powered by an electric motor 17 having a speed control 2.

The tape exiting from the measuring stage passes through a second tape alignment means 5 positioned below the measuring stage having alignment rollers 19 and polymer film stripping knives 6 aligned to strip a polymer film which forms on the tape. The second tape alignment means is positioned approximately 3 to 8 inches below the second alignment means which is sufficient to allow cooling and solidification of the molten polymer adhering to the tape.

The rheometer is attached to the extruder barrel 14 by a series of collars and spacers. For example, collar coupling 51 is connected to the rheometer by a collar 52A, a spacer 53 and a main collar 54 for maintaining the rheometer head to the extruder. A passage way 52 is provided passing through said collar coupling, collars and spacers, through which molten polymer flows. The collar and spacer assembly is held together by bolts 56 and 67.

The molten polymer flows from the extruder into a cavity 52 through which the tape moves. The cavity is contained within a rheometer head 55 positioned below the tape spool. The rheometer head consists of an external member 34A in which is a pair of internal heating plates 34 which form said cavity.

A collar 57 is provided for holding a measuring stage 8 which is held against the rheometer head by bolts 58. The thrust gauge is held against the measuring cell by bolts 59 and nuts 59A.

The thrust gauge consists of a thin metallic cylinder 32 which has an upper support collar 8A and a lower support collar 8B. Attached to the thrust gauge are conventional strain gauges 90A, 90B, 90C and 90D which are positioned 90 degrees from each other and oriented so that two oppose each other and are in vertical orientation and the other two oppose each other and are in horizontal orientation. The strain gauges are wired to form a Wheatstone Bridge. Force applied to the cylinder causes a flexing of the cylinder which is measured by the strain gauges.

The arrangement of the tape in the front portion cavity 60 is shown. The molten polymer flows from passage way 52 to fill said cavity formed by two internal heating plates 34 into which are drilled an opening 64 for a thermocoupling and an opening 61 for a heater. Below the internal heating plates and in contact thereto is the measuring cell 57. Excess polymer exits from the excess polymer port 23. The rheometer head is held to the extruder by means of bolts 67.

Figure 4:
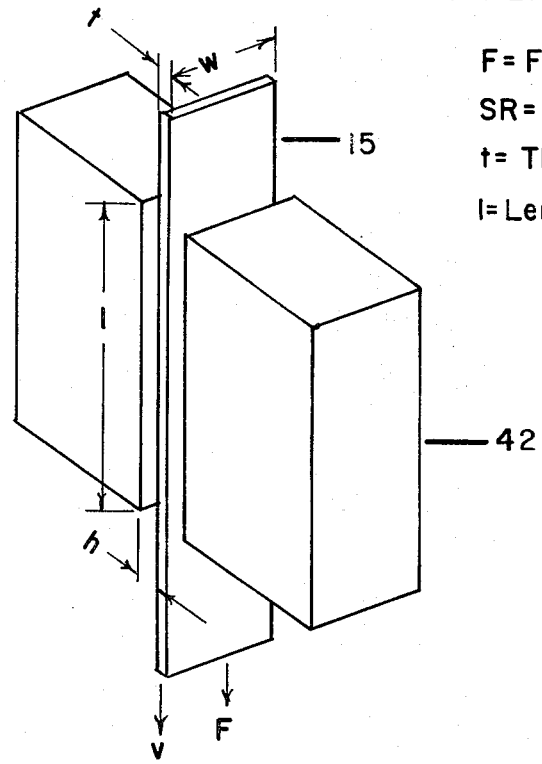
FIG. 4 is a pictoral view showing the spacial relationship of the elements of the measuring stage of the rheometer showing in FIGS. 1, 2 and 3.

In FIG. 4 a schematic of the stainless steel tape 15 is shown in the measuring slit composed of slit walls 42. Due to hydrostatic pressure of the molten polymer, the tape, having a velocity V, will be positioned in the center of the slit. The clearance between the surface of the tape and the slit wall is expressed as h. The length of the slit is l preferably 1.000 inch. The preferred dimensions of the tape are shown as follows: t the thickness of the tape preferably is 0.005 inch, and w the width of the tape preferably is 0.375 inch. The width of the slit walls u is at least 0.01 inch greater than w providing edge clearance of the tape in the slit of 0.005 inch. The force F required to pull the tape through the slit is provided by the tape drive.

The relationship between the dimensions of the slit of the measuring tape, the clearance, the velocity of the tape through the slit and the force of pull of the tape through the cell are used to calculate shear stress SS, shear rate SR, and viscosity of the molten by the formula:

FORMULA $SR = V/h$ $SS = F/2wl$ $n = SS/SR$

The thrust measuring cell is at the heart of the invention and it consists of: a thin walled cylinder 32 located in the thrust measuring stage 8 comprising an upper support member 8A and a lower support member 8B. The thrust measuring cell is supported by three bolts 59 which hold the thrust measuring cell beneath and against the normal stress cell 66 which house the quartz rod 33 and the diaphragm 63. Through the center of the stress cell is a slit through which the stainless steel tape passes. As the tape is pulled through the molten polymer, a portion of polymer adhering to the tape is pulled through the slit. Within the slit is a thin walled diaphragm 66, preferably 0.004 inch thick. This diaphragm is sensitive to lateral stress manifested by flexing of the diaphragm, thereby monitoring the normal stress produced when the tape is in motion. This flexing is measured by a strain gauge transducer capable of detecting movement of 0.0001 inch which is inserted in port 33 and in operative connection to the diaphragm.

The thin walled cylinder 32 described above operates as a compressible member strictly within its elastic limits. Bonded to the outer walls of this thin walled cylinder are strain gauges 90A, 90B, 90C and 90D, attached in the form of a full wheatstone bridge, the output signal of which is recorded electronically by a recorder.

Depending upon the polymer being characterized, the motor used to drive the stainless steel tape is conveniently a ⅛ to ¼ horse power a direct current variable speed drive electric motor capable of turning 1750 revolutions per minute with a pulling force up to 750 lbs. During operation, the pulling force required to pull the tape through the molten polymer in the measuring cell is about 10 to 100 lbs. and preferably 25 to 30 lbs. The motor is equipped with a reducer to control the speed of the tape. I have found that a double worm reducer having a 500 to 1 reduction conveniently reduces the speed of the tape to a desired 10 to 50 feet per minute.

Below the measuring stage is a polymer stripping stage 5 secured to the frame by bolts 65 and having a pair of knives 6 which strip the hardened polymer from the tape. In most cases, the tape can be used without recleaning. Preferably, the tape in the upper spool has been degreased prior to use. The polymer stripping stage consists of a lower tape alignment rollers 19.

The size of the spool can be 4 to 12 inches in diameter, and conveniently is 6 to 8 inches in diameter. The spool may be larger or smaller than this length.

The tape is prevented from unrolling by the slight resistance produced by a brake 24 against the rear hub 18A. The brake is pushed against the rear hub by a spring 24B supported by an extension 24A connected to the frame.

The brake which engages the spoon can be made of a phenolic material having some abrasion resistance which in contact with the hub of the spool or the spool itself provides a minimal braking action to prevent the tape from prematurely dispensing the tape.

The tape is preferably made of a high strength stainless steel. I have found that tapes made of the 300 series corrosion-resistant stainless steel have the requisite strength and corrosion resistance for use in my rheometer. The width and thickness of the tape is preferably and $0.005 \pm 0.0001$ respectively. In operation, the polymer flowing through the measuring cell is under about 5 to 10 pounds per square inch pressure. The temperature of the molten polymer which is kept at temperatures by two 300 to 400 watt electric cartridge heaters above the glass transition state of the polymer being studied.

The invention is a useful tool which can be mounted on an extruder to provide continuous viscosity properties of the molten polymer being extruded. In this embodiment, the extruder would be adapted to provide a small side stream of polymer to the rheometer and thus supply a continuous flow of polymer melt to the device for continuous measurement of viscosity while extruding polymer. My rheometer can be used to provide the properties of a continuous supply of polymer melt to a measuring cell.

In theory, a continuous supply of polymer melt established in the inlet is pulled by the tape as a thin film through the measuring zone. The molten polymer adheres to both sides of the tape. The viscosity drag imposes a thrust upon this zone and the force of the shear stress can be measured. Any pressure losses at the slit have been isolated. The losses are not measured and do not enter into any calculations.

Normal stress is induced in viscoelastic flow and the lateral component of the normal stress, whether tension or compression is determined in a similar manner and simultaneously in the same velocity field as that for the viscosity measurement with a thin film continuously supplied from fresh melt.

The thermal gradient is neglible, with 7 seconds being the average time required per determination.

Figure 5:
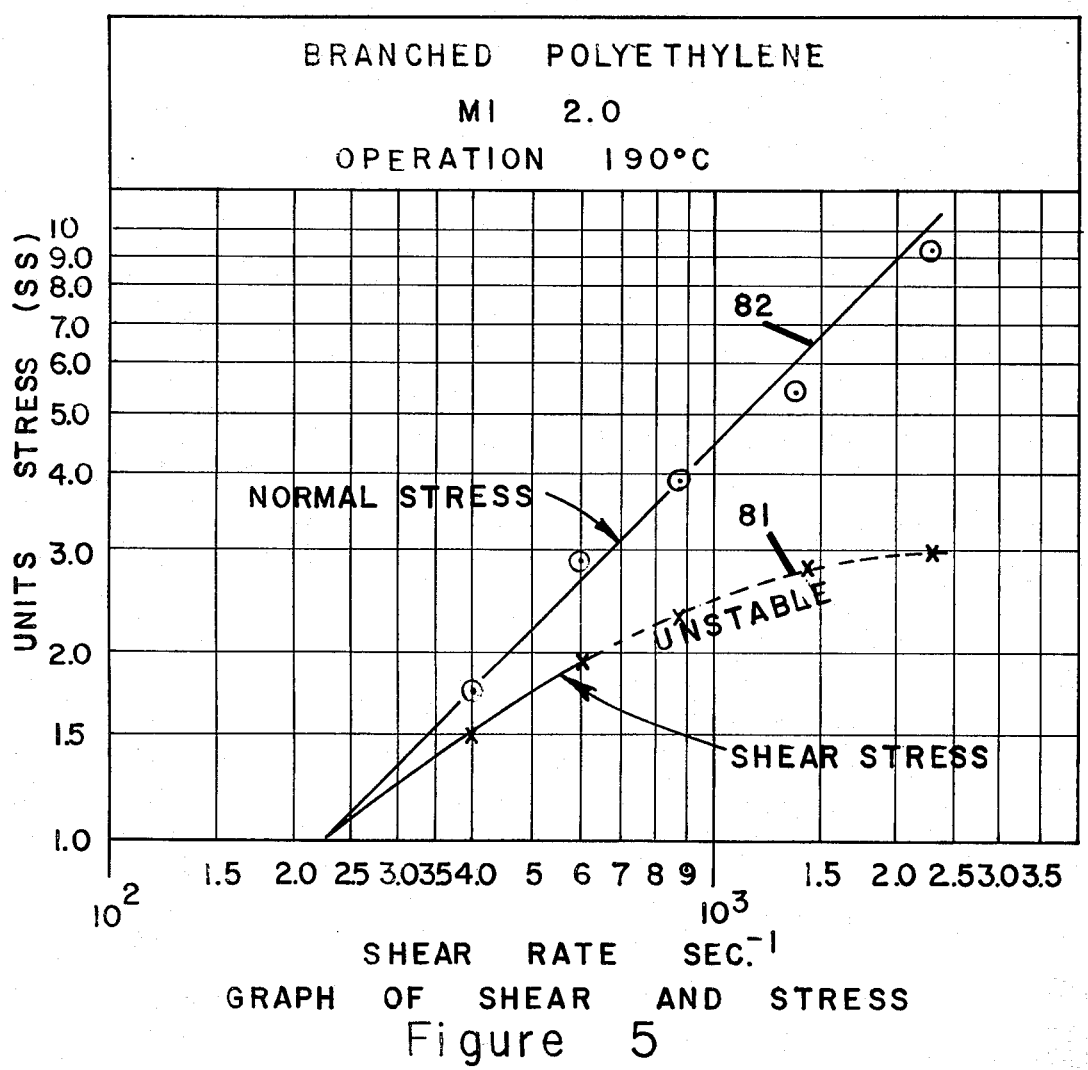
FIG. 5 is a graph of the shear stress and normal stress data determined by use of the device of this invention on a sample of branded polyethylene having a melt index (MI) of 2.0.

FIG. 5 is a plot of the normal stress 82 and shear stress 81 obtained at 190° C. and varying shear rates on branded polyethylene having a melt index (MI) of 2 obtained using the rheometer disclosed herein. It is observed that the shear stress measurement passes into an unstable region (represented by a dotted line). This unstable region is believed to be due to excess tape speed causing excess shear.

In FIGS. 6 and 7, the measuring cell is shown in greater detail. The measuring cell measures the change in dimension of the tube 8 which occurs as a result of the forece applied to it as the tape is pulled through the molten polymer.

The diameter of the tube expands and/or contracts an extremely small amount due to the force applied to it, and this microchange in dimension is detected and measured by strain gauges 90A, 90B, 90C and 90D.

In order to analyize a polymer the extruder is heated to a desired temperature and polymer is extruded through the channel 52A at a flow rate of 1 oz. to 600 oz. per minute. The polymer flows through a pentagon cell cavity 60 having a lower slit above the measuring stage. As stated above, the tape is pulled through the molten polymer and out of the cavity, through the slit and past a thin diaphragm 63. The amount of diaphragm bulge depends upon the viscosity of the polymer. The distortion is measured by a suspended wire strain gauge 33 or a diaphragm pressure transducer (not shown).

The rheometer is operated as follows.

A supply of thin stainless steel tape 5 mils thick and 0.375 inches wide is provided on a spool containing about 300 feet. The tape is contained in a heated chamber above the measuring stage. The tape is preferably heated to the same temperature as the molten polymer. The heated tape is fed through guide rolls into the polymer pick up zone through a measuring chamber then over clean up knives which strip a polymer film coating which has been formed off the tape, then through guide rolls to a take up spool, preferably the measuring zone consists of a rectangular slit 1 inch in length, 25 mils in thickness and a width of 0.395 inches. The diaphragm is positioned in the wall of the slit.

While the thickness of the tape and the width of the slit through which it is drawn may be varied greatly, the above dimensions are convenient for the size of the apparatus of this invention. In order to eliminate variations in the data obtained, the tape entering the measuring zone and the polymer melt are maintained at the same temperature. The knife polymer film removal tools provide film samples for further examination and clean steel tape for eventual substitution for the then empty upper spool.

I claim:

1. A sliding film rheometer for measuring the viscosity of a molten polymer by simultaneously measuring in the same shear field shear stress and normal stress comprising:
   (i) a shear stress and normal stress producing member consisting of a tape having a rectangular shaped cross-section;
   (ii) a measuring cell containing molten polymer heated to a constant temperature having an inlet orifice and a rectangularly shaped outlet slit, said rectangular shaped outlet slit being adapted to be slightly larger than the cross-section of said tape;
   (iii) means for pulling, at a controlled rate of speed, said tape through said inlet orifice, then through said molten polymer, and then through said rectangular shaped outlet slit, thereby producing shear stress and normal stress; and
   (iv) measuring means operatively connected to said measuring cell for simultaneously measuring said shear stress and normal stress produced in said molten polymer.

2. The rheometer of claim 1 wherein said tape has a thickness of 0.0049 to 0.0051 inch and a width of 0.375 inch, and said slit with a clearance of at least 0.015 inch and a length of 0.400 to 1.0 inch.

3. The rheometer of claim 1 wherein the tape is composed of metal.

4. The rheometer of claim 1 wherein the tape is pulled through the slit at a speed one to one hundred inches per minute.

5. A process for measuring the viscosity of a molten polymer comprising measuring in the same shear field shear stress and normal stress produced by pulling a tape at a controlled rate of speed through a measuring cell containing molten polymer heated to a constant temperature and thereafter through a slit operatively connected to said measuring cell having dimensions slightly larger than said tape.

6. The process of claim 5 wherein said tape has a thickness of 0.0049 to 0.0051 inch and a width of 0.375 inch, and said slit has a cross-section having a clearance of 0.010 inch and a length of 0.400 to 1.0 inch.

* * * * *